United States Patent [19]

Houlihan

[11] 3,947,460

[45] Mar. 30, 1976

[54] 5-HYDROXY-5-SUBSTITUTED PHENYL-PYRROLIDONES AND PIPERIDINONES

[75] Inventor: William J. Houlihan, Mountain Lakes, N.J.

[73] Assignee: Sandoz, Inc., E. Hanover, N.J.

[22] Filed: Aug. 8, 1974

[21] Appl. No.: 495,861

Related U.S. Application Data

[63] Continuation-in-part of Ser. No. 483,552, June 27, 1974, abandoned, which is a continuation-in-part of Ser. No. 468,377, May 9, 1974, abandoned, which is a continuation-in-part of Ser. No. 417,374, Nov. 19, 1973, abandoned.

[52] U.S. Cl.... 260/293.76; 260/326.5 FL; 260/463; 260/558 D; 260/558 R; 424/267; 424/274
[51] Int. Cl.². ............... C07D 207/26; C07D 211/76
[58] Field of Search ............... 260/326.5 FL, 293.76

[56] References Cited

UNITED STATES PATENTS

| | | | |
|---|---|---|---|
| 3,073,834 | 1/1963 | Bortnick et al. | 260/326.5 X |
| 3,077,478 | 2/1963 | Bortnick et al. | 260/326.5 X |
| 3,117,975 | 1/1964 | Bortnick et al. | 260/326.5 X |

OTHER PUBLICATIONS

Ratto et al., T. Pharm. Sci., 53, 480–483 (1964).
Laurence, Chem. Abs., Vol. 70, 77089p (1969).

*Primary Examiner*—Donald G. Daus
*Assistant Examiner*—Mark L. Berch
*Attorney, Agent, or Firm*—Gerald D. Sharkin; Robert S. Honor

[57] ABSTRACT

5-hydroxy-5-substituted phenyl-pyrrolidones and piperidinones, 3.g., 5-hydroxy-1-methyl-5-(m-trifluoromethylphenyl)pyrrolidone, are useful as sedative-hypnotic agents and minor tranquilizers.

5 Claims, No Drawings

5-HYDROXY-5-SUBSTITUTED PHENYL-PYRROLIDONES AND PIPERIDINONES

This application is a continuation-in-part of copending application Ser. No. 483,552 now abandoned, filed June 27, 1974, which in turn is a continuation-in-part of copending application Ser. No. 468,377 now abandoned, filed May 9, 1974, which in turn is a continuation-in-part of copending application Ser. No. 417,374, filed Nov. 19, 1973 now abandoned.

This invention relates to pyrrolidone and piperidinone derivatives which exhibit sedative-hypnotic and minor tranquilizer activity. In particular, it relates to 5-hydroxy-5-substituted phenyl-pyrrolidones and piperidinones, their preparation and intermediates thereof.

The compounds of this invention may be represented by the following structural formula

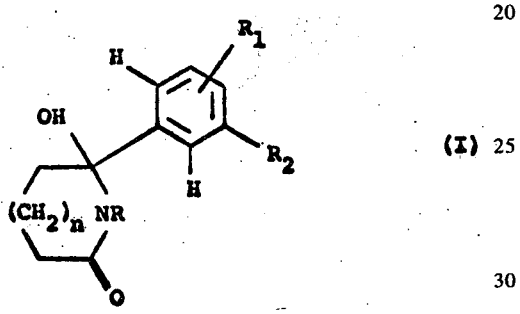

(I)

where
R is hydrogen or lower alkyl, i.e., lower alkyl having 1 to 4 carbon atoms, e.g., methyl, ethyl, isopropyl and the like,
$R_1$ is hydrogen or halo having an atomic weight of about 19 to 36,
$R_2$ is methyl or trifluoromethyl, and
n is 0 or 1.

The compounds of formula (I) may be prepared according to the following reaction scheme A:

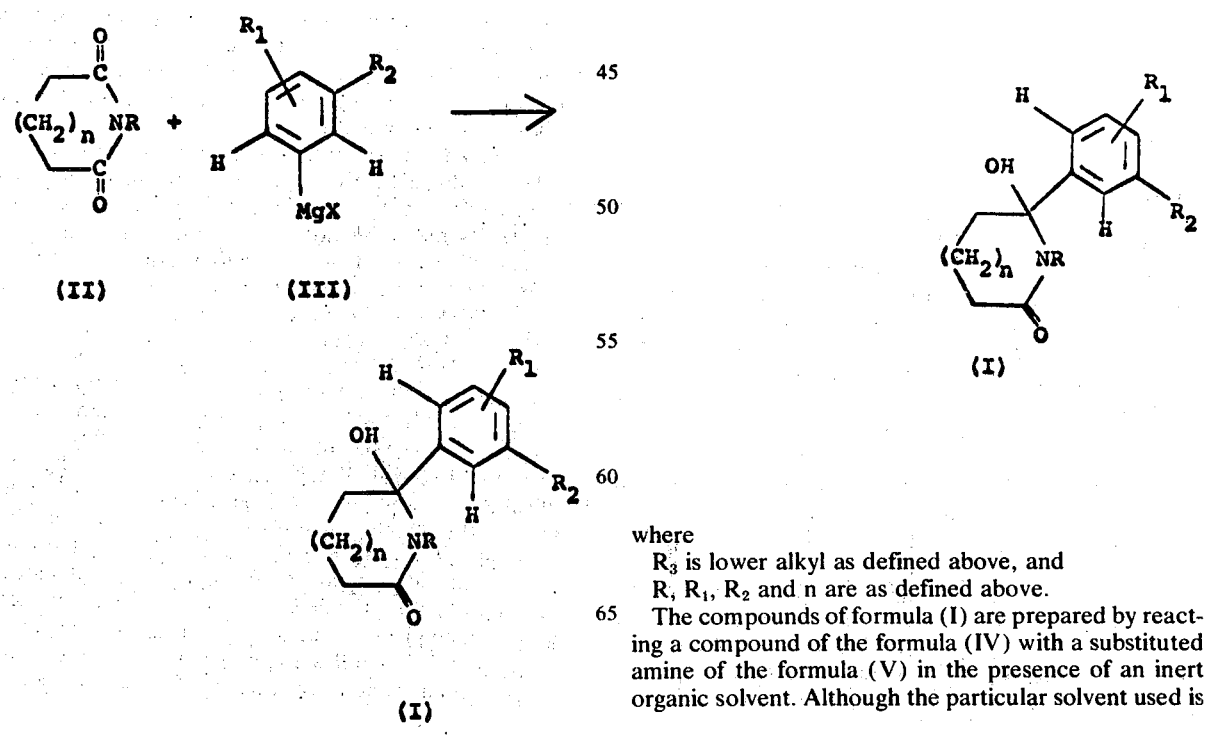

where
X represents halo having an atomic weight of about 35 to 80, and
R, $R_1$, $R_2$ and n are as defined above.

The compounds of formula (I) are prepared by reacting a compound of the formula (II) with a Grignard reagent of the formula (III) in the presence of an inert organic solvent. Although the particular solvent used is not critical, the preferred solvents are the ethers, such as diethylether, tetrahydrofuran and the like, alkanes having 6 to 12 carbon atoms, e.g., hexane, heptane and the like, or the aromatic hydrocarbons such as benzene, toluene, xylene and the like, preferably benzene. The temperature of the reaction is not critical but it is preferred that the reaction be carried out at a temperature between about 35° to 150°C., preferably the reflux temperature of the solvent. The reaction may be run from about 2 to 10 hours, preferably from about 4 to 6 hours. The product is recovered using conventional techniques, e.g., crystallization.

The compounds of formula (I) may also be prepared according to the following reaction scheme B:

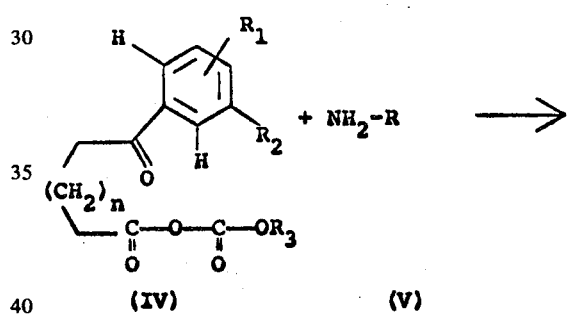

where
$R_3$ is lower alkyl as defined above, and
R, $R_1$, $R_2$ and n are as defined above.

The compounds of formula (I) are prepared by reacting a compound of the formula (IV) with a substituted amine of the formula (V) in the presence of an inert organic solvent. Although the particular solvent used is not critical, the preferred solvents are the ethers such as diethylether, tetrahydrofuran, dioxane and the like, the aromatic hydrocarbons, e.g., benzene, toluene and the like, or the halogenated hydrocarbons such as chloroform, the latter being especially preferred. The temperature of the reaction is not critical, but it is preferred that the reaction be carried out at a temperature between about −20° to 100°C., preferably between about −10° to 50°C. The reaction may be run from about 10 to 48 hours, preferably from about 16 to 24 hours. The product is recovered using conventional techniques, e.g., crystallization.

The compounds of formula (IV) are prepared according to the following reaction scheme:

(VI) + Cl-C(O)-OR$_3$ (VII) $\xrightarrow{\text{acid binding agent}}$ (IV)

where
R, R$_1$, R$_2$, R$_3$ and n are as defined above.

The compounds of formula (IV) are prepared by reacting a compound of the formula (VI) with an alkyl chloroformate of the formula (VII) in the presence of an acid binding agent and an inert organic solvent. The acid binding agents which can be employed in this particular reaction include the trialkylamines such as trimethylamine, triethylamine and the like, or pyridine, preferably triethylamine. Although the particular solvent used is not critical, the preferred solvents are the ethers such as diethylether, tetrahydrofuran, dioxane and the like, the aromatic hydrocarbons such as benzene or toluene, or halogenated hydrocarbons such as chloroform, the latter being especially preferred. The temperature of the reaction is not critical, but it is preferred that the reaction be carried out at a temperature between about −20° to 100°C., preferably between about −10° to 50°C. The reaction may be run from about 1 to 8 hours, preferably 2 to 3 hours. The product is recovered using conventional techniques, e.g., crystallization.

The compounds of formula (I) may also exist in the form of their tautomeric equivalents such as represented by the following structural formula:

(Ia)

where
R, R$_1$, R$_2$ and n are as defined above.

The predominant tautomer is believed to depend on the nature of R. When R is branched chain lower alkyl, e.g., isopropyl or t-butyl, then the tautomeric form of formula (Ia) will predominate. When R is straight chain lower alkyl, then the tautomeric form of compound (I) will predominate. It is to be noted that both tautomeric forms, i.e., the compounds of formulae (I) and (Ia), are included within the scope of this invention.

Many of the compounds of formulae (II), (III), (V), (VI), and (VII) are known and may be prepared by methods described in the literature. The compounds of formulae (II), (III), (V), (VI) and (VII) not specifically disclosed may be prepared by analogous methods from known starting materials.

The compounds of formulae (I) and (Ia) possess pharmacological activity. In particular, the compounds are useful as central nervous system depressants, especially as sedative-hypnotics and minor tranquilizers as indicated by (1) their ability to produce docility in behavior tests in mice given 25 to 200 mg/kg of animal body weight, i.p. of the test compound according to the 30-word adjective check sheet system basically as described by Irwin S. (Gordon Research Conference, Medicinal Chemistry, 1959) and Chen (Symposium on Sedative and Hypnotic Drugs, Williams and Wilkins, 1954); (2) by their ability to antagonize chronic convulsions and death in mice given 50 to 250 mg/kg i.p. of N-sulfamoylazepine; (3) by the hexobarbital reinduction method of (Winter, J. Pharmacol and Exp. Therap., 94, 7-11, 1948) in which the reinduction of anesthesia after recovery from hexobarbital induced anesthesia is used to determine sedative-hypnotic activity in mice given 70 mg/kg of animal body weight, i.p. of hexobarbital followed immediately after the mice regain their righting reflexes by 25 to 200 mg/kg of animal body weight, i.p. of the test compound; (4) by their ability to reduce conflicts as defined in the Geller Conflict test (Irving Geller, Psychopharmacologia, Volumne I, Pages 42–492, 1960); and (5) as indicated in Cebus monkey using chlonically implanted electrodes. Brain readings are obtained via a ten or sixteen channel electroencephalograph. For the recording sessions, the monkeys are restrained by neck and waist plates in chairs in full side observation cages at the same time every night for thirteen and one half hours Monday through Thursday. Gross behavior is monitored via closed circuit television and video tape recordings. The compounds of formula (I) and (Ia) are administered p.o. at a dosage of from about 1.8 to about 30 mg/kg immediately on placing the monkey in the observation cages with at least seven days intervening between drug administration. Physiological saline is administered via a similar route and at the same times on all control runs. Control data are collected at least three days per week and accumulated to give control data for fifteen sessions per monkey. Data from each session are statistically compared via computer analysis to the previous 5–15 control sessions for the particular animal, with particular emphasis given to the following phases of the sleep-wakefulness cycle: resting awake, light sleep, deep sleep, paradoxical (REM) sleep, "pseudo-" paradoxical sleep, latency to onset of deep sleep, and latency to onset of first epoch of paradoxical sleep.

For such usage, the compounds of formula (I) and (Ia) may be administered orally or parenterally as such or admixed with conventional pharmaceutical carriers. They may be administered orally in such forms as tablets, dispersible powders, granules, capsules, syrups and elixirs, and parenterally as solutions, e.g., a sterile injectable aqueous solution. The compositions for oral use may contain one or more conventional adjuvants, such as sweetening agents, in order to provide an elegant and palatable preparation. Tablets may contain the active ingredient in admixture with conventional pharmaceutically acceptable excipients, e.g., inert diluents, such as calcium carbonate, sodium carbonate, lactose, and talc, granulating and disintegrating agents, e.g., starch and alginic acid, binding agents, e.g., starch, gelatin and acacia, and lubricating agents, e.g, magnesium stearate, stearic acid and talc. The tablets may be uncoated or coated by known techniques to delay disintegration and absorption in the gastrointestinal tract and thereby provide a sustained action over a longer period. Similarly, suspensions, syrups, and elixirs, may contain the active ingredient in admixture with any of the conventional excipients utilized for the preparation of such compositions, e.g., suspending agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The injectable compositions are formulated as known in the art. All these pharmaceutical preparations may contain up to about 90% of the active ingredient in combination with the carrier or adjuvant.

For the above-indicated use as a minor tranquilizer, the dosage of compounds (I) and (Ia) will vary depending upon the mode of administration utilized and the particular compound employed. However, in general, satisfactory results are obtained when the compounds are administered at a daily dosage of from about 1 milligram to about 100 milligrams per kilogram of animal body weight p.o. This daily dosage is preferably given in divided doses, e.g., 2 to 4 times per day, or in sustained release form. For most large mammals, the total daily dosage is from about 75 milligrams to 1500 milligrams and dosage forms suitable for internal administration comprise from about 18 milligrams to about 750 milligrams of the compound in admixture with a solid or liquid pharmaceutical carrier or diluent.

The sedative-hypnotic effective dosage of the compounds of formulae (I) and (Ia) will vary depending on the particular compound employed. However, in general, satisfactory results are obtained when the compounds are administered orally at a daily dosage of from about 2 milligrams to about 200 milligrams per kilogram of animal body weight p.o., typically given in a single dose at bedtime. For most large mammals, the total daily dosage is from about 150 milligrams to about 1500 milligrams, preferably in a single dose at bedtime.

Tablets and capsules containing the ingredients below may be prepared by conventional techniques and are useful as central nervous system depressants at a dose of one tablet or capsule 2 to 4 times a day.

| Ingredient | Weight (mg.) |
|---|---|
| 5-hydroxy-1-methyl-5-(m-trifluoromethylphenyl)pyrrolidone | 100 |
| inert solid diluent (starch, lactose, kaolin) | 200 |

EXAMPLE 1

5-Hydroxy-1-methyl-5-(m-trifluoromethylphenyl)pyrrolidone.

To a Grignard prepared from 37 g. (0.16 mole) of 3-bromobenzotrifluoride and 3.7 g. (0.16 mole) of magnesium turnings in 100 ml. of dry diethylether, there is added dropwise over a period of about 10 minutes 12.2 g. (0.11 mole) of N-methylsuccinimide in 100 ml. of dry benzene. The resulting mixture is stirred and refluxed for about 4 hours and then allowed to stand overnight at room temperature. Stirring is resumed and 40 ml. of 50% sulfuric acid is added dropwise at such a rate to maintain a gentle reflux. After an additional 0.5 hours, the water layer is separated and washed twice with 50 ml. of benzene. The organic layers are combined and washed with 50 ml. of sodium carbonate and then twice more with 50 ml. of water. The resulting layer is dried over anhydrous magnesium sulfate, filtered and evaporated in vacuo. The resulting residue is crystallized from methylene chloride/hexane to give 5-hydroxy-1-methyl-5-(m-trifluoromethylphenyl)pyrrolidone; m.p. 137°– 139°C.

Following the above procedure and using in place of 3-bromo-benzotrifluoride an equivalent amount of a 2-chloro-5-bromobenzotrifluoride, or b 2-fluoro-5-bromobenzotrifluoride, there is obtained a   5-hydroxy-1-methyl-5-(4-chloro-m-trifluoromethylphenyl) pyrrolidone, or b   5-hydroxy-1-methyl-5-(4-fluoro-m-trifluoromethylphenyl) pyrrolidone.

Again following the above procedure and using in place of N-methyl succinimide, an equivalent amount of c N-ethylsuccinimide, d succinimide, e N-methylglutarimide, or
f glutarimide,
there is obtained
c  5-hydroxy-1-ethyl-5-(m-trifluoromethylphenyl)pyrrolidone,
d  5-hydroxy-5-(m-trifluoromethylphenyl)pyrrolidone,
e  6-hydroxy-1-methyl-6-(m-trifluoromethylphenyl)piperidinone,
or
f  6-hydroxy-6-(m-trifluoromethylphenyl)piperidinone, respectively.

EXAMPLE 2

5-Hydroxy-1-methyl-5-(m-tolyl)pyrrolidone.

To a Grignard prepared from 27.3g (0.16 mole) of 3-bromotoluene and 3.7 g. (0.16 mole) of magnesium turnings in 100 ml. of dry diethylether, there is added dropwise over a period of about 10 minutes 12.2 g. (0.11 mole) of N-methylsuccinimide in 100 ml. of dry benzene. The resulting mixture is stirred and refluxed for about 4 hours and then allowed to stand overnight at room temperature. Stirring is resumed and 40 ml. of 50% sulfuric acid is added dropwise at such a rate to maintain a gentle reflux. After an additional 0.5 hours, the water layer is separated and washed twice with 50 ml. of benzene. The organic layers are combined and washed with 50 ml. of sodium carbonate and then twice more with 50 ml. of water. The resulting layer is dried over anhydrous magnesium sulfate, filtered and evaporated in vacuo. The resulting residue is crystallized from methylene chloride/hexane to give 5-hydroxy-1-methyl-5-(m-tolyl) pyrrolidone; m.p. 128°–130°C.

Following the above procedure and using in place of 3-bromotoluene an equivalent amount of
a 2-chloro-5-bromotoluene, or
b 2-fluoro-5-bromotoluene,
there is obtained
a  5-hydroxy-1-methyl-5-(4-chloro-m-tolyl)pyrrolidone, or
b  5-hydroxy-1-methyl-5-(4-fluoro-m-tolyl)pyrrolidone.

Again following the above procedure and using in place of N-methylsuccinimide, an equivalent amount of
c N-ethylsuccinimide,
d N-methylglutarimide, or
e N-ethylglutarimide,
there is obtained
c 5-hydroxy-1-ethyl-5-(m-tolyl)pyrrolidone,
d 6-hydroxy-1-methyl-6-(m-tolyl)piperidinone, or
e 6-hydroxy-1-ethyl-(m-tolyl)piperidinone, respectively.

EXAMPLE 3

5-Hydroxy-1-methyl-5-(m-trifluoromethylphenyl)pyrrolidone.

To a mixture of 24.5 g. 3-(m-trifluoromethylbenzoyl)propionic acid (0.10 mole) and 10.1 g. triethylamine (0.10 mole) in 250 ml. of chloroform cooled to 0°C., there is added dropwise 10.8 g. (0.10 mole) of ethyl chloroformate at such a rate that the critical temperature does not exceed 10°C. The reaction is stirred for 2 ½ hours to obtain the mixed anhydride of 3-benzoylpropionic acid which is then treated with 3.1 g. of methylamine (0.10 mole) in 100 ml. of chloroform. The cooling apparatus is removed and the reaction is stirred for about 20 hours. The chloroform layer is then washed with 50 ml. of water, 100 ml. 1N hydrochloric acid, 100 ml. saturated sodium chloride solution, dried over anhydrous magnesium sulfate, filtered, and concentrated in vacuo. The resulting residue is crystallized from methylene chloride/hexane to give 5-hydroxy-1-methyl-5-(m-trifluoromethylphenyl)pyrrolidone; m.p. 137°–139°C.

Following the above procedure and using in place of 3-(m-trifluoromethylbenzoyl)propionic acid an equivalent amount of
a. 3-(4-chloro-m-trifluoromethylbenzoyl)propionic acid,
b. 3-(4-fluoro-m-trifluoromethylbenzoyl)propionic acid, or
c. 3-(m-trifluoromethylbenzoyl)butyric acid,
there is obtained
a  5-hydroxy-1-methyl-5-(4-chloro-m-trifluoromethylphenyl) pyrrolidone,
b  5-hydroxy-1-methyl-5-(4-fluoro-m-trifluoromethylphenyl) pyrrolidone, or
c  5-hydroxy-1-methyl-5-(m-trifluoromethylphenyl)piperidinone.

Again following the above procedure but using in place of methylamine an equivalent amount of
d ammonia, or
e ethylamine,
there is obtained
d. 5-hydroxy-5-(m-trifluoromethylphenyl)pyrrolidone, or
e. 5-hydroxy-1-ethyl-5-(m-trifluoromethylphenyl)pyrrolidone, respectively.

EXAMPLE 4

5-Hydroxy-1-methyl-5-(m-tolyl)pyrrolidone.

To a mixture of 24.5 g. 3-(m-toluoyl)propionic acid (0.10 mole) and 10.1 g. triethylamine (0.10 mole) in 250 ml. of chloroform cooled to 0°C., there is added dropwise 10.8 g. (0.10 mole) of ethyl chloroformate at such a rate that the critical temperature does not exceed 10°C. The reaction is stirred for 2 ½ hours to obtain the mixed anhydride of 3-benzoylpropionic acid which is then treated with 3.1 g. of methylamine (0.10 mole) in 100 ml. of chloroform. The cooling apparatus is removed and the reaction is stirred for about 20 hours. The chloroform layer is then washed with 50 ml. of water, 100 ml. 1N hydrochloric acid, 100 ml. saturated sodium chloride solution, dried over anhydrous magnesium sulfate, filtered, and concentrated in vacuo. The resulting residue is crystallized from methylene chloride/hexane to give 5-hydroxy-1-methyl-5-(m-tolyl) pyrrolidone; m.p. 128°–130°C.

Following the above procedure and using in place of 3-(m-trifluoromethylbenzoyl)propionic acid an equivalent amount of
a 3-(4-chloro-m-toluoyl)propionic acid,
b 3-(4-fluoro-m-toluoyl)propionic acid, or
c 3-(m-toluoyl)butyric acid,
there is obtained
a  5-hydroxy-1-methyl-5-(4-chloro-m-tolyl)pyrrolidone,
b  5-hydroxy-1-methyl-5-(4-fluoro-m-tolyl)pyrrolidone, or
c 5-hydroxy-1-methyl-5-(m-tolyl)piperidinone.

Again following the above procedure but using in place of methylamine an equivalent amount of
d. ammonia, or
e. ethylamine there is obtained
  d. 5-hydroxy-5-(m-tolyl)pyrrolidone, or
  e. 5-hydroxy-1-ethyl-5-(m-tolyl)pyrrolidone, respectively.

What is claimed is:
1. A compound of the formula:

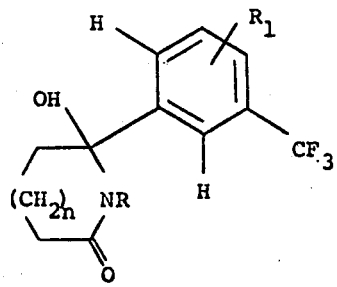

where
  R is hydrogen or lower alkyl having 1 to 4 carbon atoms,
  $R_1$ is hydrogen or halo having an atomic weight of about 19 to 36, and
  n is 0 or 1.
2. A compound according to claim 1 in which R represents lower alkyl, $R_1$ represents hydrogen and n is 0.
3. The compound of claim 1 which is 5-hydroxy-1-methyl-5-(m-trifluoromethylphenyl)pyrrolidone.
4. The compound of claim 1 which is 5-hydroxy-1-ethyl-5-(m-trifluoromethylphenyl)pyrrolidone.
5. The compound of claim 1 which is 5-hydroxy-5-(m-trifluoromethylphenyl)pyrrolidone.

* * * * *